(12) United States Patent
Gephart et al.

(10) Patent No.: US 10,485,600 B2
(45) Date of Patent: Nov. 26, 2019

(54) SURGICAL CABLE TENSIONER

(71) Applicant: A&E Advanced Closure Systems, LLC, Los Angeles, CA (US)

(72) Inventors: Matthew P. Gephart, Marquette, MI (US); Peter Didyk, Marquette, MI (US)

(73) Assignee: A&E Advanced Closure Systems, LLC, Los Angeles, CA (US)

( * ) Notice: Subject to any disclaimer, the term of this patent is extended or adjusted under 35 U.S.C. 154(b) by 316 days.

(21) Appl. No.: 15/645,029

(22) Filed: Jul. 10, 2017

(65) Prior Publication Data

US 2018/0029824 A1 Feb. 1, 2018

Related U.S. Application Data

(60) Provisional application No. 62/368,753, filed on Jul. 29, 2016.

(51) Int. Cl.
*A61B 17/88* (2006.01)
*B65H 59/20* (2006.01)

(52) U.S. Cl.
CPC ......... *A61B 17/8869* (2013.01); *B65H 59/20* (2013.01); *A61B 17/8861* (2013.01); *B65H 2701/3918* (2013.01)

(58) Field of Classification Search
CPC .. A61B 17/88; A61B 17/8861; A61B 17/8869
See application file for complete search history.

(56) References Cited

U.S. PATENT DOCUMENTS

| 1,988,534 | A | 1/1935 | Joseph |
| 2,002,977 | A | 5/1935 | Carr |
| 2,557,877 | A | 6/1951 | Kluson |
| 3,959,960 | A | 6/1976 | Santos |
| 4,050,464 | A | 9/1977 | Hall |

(Continued)

FOREIGN PATENT DOCUMENTS

| AU | 743254 | 1/2002 |
| CN | 201260694 Y | 6/2009 |

(Continued)

OTHER PUBLICATIONS

U.S. Appl. No. 62/286,062, filed Jan. 22, 2016. Robert A. Mitchell.

(Continued)

*Primary Examiner* — Eric S Gibson
(74) *Attorney, Agent, or Firm* — Fitch, Even, Tabin & Flannery LLP

(57) ABSTRACT

In accordance with one aspect of the present disclosure, an instrument for tensioning a surgical cable is provided that includes a rotary tensioner that is rotatable in a tensioning rotary direction to apply tension to the surgical cable. The instrument further includes a body supporting the rotary tensioner, a pawl portion of the body configured to be received at least partially in a recess of a ratchet gear of the rotary tensioner, and a living hinge portion of the body supporting the pawl portion. The living hinge portion is configured to permit the pawl portion to be shifted out of the recess and shifted into an adjacent recess of the ratchet gear with turning of the rotary tensioner in the tensioning rotary direction

20 Claims, 12 Drawing Sheets

(56) References Cited

U.S. PATENT DOCUMENTS

| | | | |
|---|---|---|---|
| 4,184,784 A | 1/1980 | Killian | |
| 4,269,180 A | 5/1981 | Dall | |
| 4,327,715 A | 5/1982 | Corvisier | |
| 4,583,541 A | 4/1986 | Barry | |
| 4,959,065 A | 9/1990 | Arnett | |
| 4,966,600 A | 10/1990 | Songer | |
| 5,015,248 A | 5/1991 | Burstein | |
| 5,139,498 A | 8/1992 | Astudillo Ley | |
| 5,312,410 A | 5/1994 | Miller | |
| 5,395,374 A | 3/1995 | Miller | |
| 5,415,658 A | 5/1995 | Kilpela | |
| 5,449,361 A | 9/1995 | Preissman | |
| 5,456,722 A | 10/1995 | McLeod | |
| 5,514,091 A | 5/1996 | Yoon | |
| 5,522,827 A | 6/1996 | Combs | |
| 5,536,270 A | 7/1996 | Songer | |
| 5,541,380 A | 7/1996 | Ogden | |
| 5,568,865 A | 10/1996 | Mase | |
| 5,569,253 A | 10/1996 | Farris | |
| 5,578,057 A | 11/1996 | Wenstrom | |
| 5,649,927 A | 7/1997 | Kilpela | |
| 5,660,091 A | 8/1997 | Stone | |
| 5,702,399 A | 12/1997 | Kilpela | |
| 5,752,959 A | 5/1998 | Korhonen | |
| 5,755,704 A | 5/1998 | Lunn | |
| 5,810,825 A | 9/1998 | Huebner | |
| 5,849,012 A | 12/1998 | Abboudi | |
| 5,902,305 A * | 5/1999 | Beger | A61B 17/8869 606/103 |
| 5,908,421 A | 6/1999 | Beger | |
| 5,935,130 A * | 8/1999 | Kilpela | A61B 17/8869 606/103 |
| 5,935,133 A * | 8/1999 | Wagner | A61B 17/82 606/103 |
| 5,941,881 A | 8/1999 | Barnes | |
| 6,017,347 A | 1/2000 | Huebner | |
| 6,077,268 A | 6/2000 | Farris | |
| 6,086,590 A | 7/2000 | Margulies | |
| 6,099,527 A | 8/2000 | Hochschuler | |
| 6,120,506 A | 9/2000 | Kohrs | |
| 6,123,709 A | 9/2000 | Jones | |
| 6,277,120 B1 | 8/2001 | Lawson | |
| 6,342,068 B1 | 1/2002 | Thompson | |
| 6,378,289 B1 * | 4/2002 | Trudeau | A61B 17/8861 24/134 R |
| 6,387,099 B1 | 5/2002 | Lange | |
| 6,398,787 B1 | 6/2002 | Itoman | |
| 6,399,886 B1 | 6/2002 | Avellanet | |
| 6,454,770 B1 | 9/2002 | Klaue | |
| 6,475,220 B1 | 11/2002 | Whiteside | |
| 6,494,907 B1 | 12/2002 | Bulver | |
| 6,520,965 B2 | 2/2003 | Chervitz | |
| 6,575,913 B1 | 6/2003 | Woolley | |
| 6,605,091 B1 | 8/2003 | Iwanski | |
| 6,629,975 B1 | 10/2003 | Kilpela | |
| 6,730,091 B1 | 5/2004 | Pfefferle | |
| 6,832,532 B2 | 12/2004 | Kilpela | |
| 6,872,210 B2 | 3/2005 | Hearn | |
| 7,052,499 B2 | 5/2006 | Steger | |
| 7,156,847 B2 | 1/2007 | Abramson | |
| 7,207,993 B1 | 4/2007 | Baldwin | |
| 7,229,444 B2 | 6/2007 | Boyd | |
| 7,250,054 B2 | 7/2007 | Allen | |
| 7,494,461 B2 | 2/2009 | Wells | |
| 7,635,365 B2 | 12/2009 | Ellis | |
| 7,695,501 B2 | 4/2010 | Ellis | |
| 7,785,355 B2 | 8/2010 | Mohr | |
| 7,803,176 B2 | 9/2010 | Teague | |
| 8,282,675 B2 | 10/2012 | Maguire | |
| 8,298,247 B2 | 10/2012 | Sterrett | |
| 8,313,517 B2 | 11/2012 | Mohr | |
| 8,337,497 B2 | 12/2012 | Deslauriers | |
| 8,372,123 B2 | 2/2013 | Smisson, III | |
| 8,460,295 B2 | 6/2013 | McClellan | |
| 8,460,345 B2 | 6/2013 | Steger | |
| 8,783,671 B2 | 7/2014 | Ranieri | |
| 8,840,735 B2 | 9/2014 | Schaffer | |
| 8,984,720 B2 | 3/2015 | Gephart | |
| 9,265,543 B2 | 2/2016 | Gephart | |
| 9,333,021 B2 * | 5/2016 | Gephart | A61B 17/842 |
| 9,510,822 B2 | 12/2016 | Poucher | |
| 9,510,882 B2 | 12/2016 | Dell'Oca | |
| 9,561,064 B2 * | 2/2017 | Goodwin | A61B 17/842 |
| 10,314,635 B2 * | 6/2019 | Gephart | A61B 17/8869 |
| 2002/0072753 A1 | 6/2002 | Cohen | |
| 2002/0177861 A1 | 11/2002 | Sugiyama | |
| 2003/0153947 A1 | 8/2003 | Koseki | |
| 2004/0138666 A1 | 7/2004 | Molz, IV | |
| 2004/0199169 A1 * | 10/2004 | Koons | A61B 17/8861 606/103 |
| 2005/0171547 A1 | 8/2005 | Aram | |
| 2005/0177179 A1 * | 8/2005 | Baynham | A61B 17/82 606/151 |
| 2006/0089646 A1 | 4/2006 | Bonutti | |
| 2006/0155328 A1 | 7/2006 | Foerster | |
| 2006/0167464 A1 | 7/2006 | Allen | |
| 2006/0271060 A1 | 11/2006 | Gordon | |
| 2006/0287653 A1 | 12/2006 | Rhyne | |
| 2007/0225715 A1 | 9/2007 | Deffenbaugh | |
| 2008/0195145 A1 | 8/2008 | Bonutti | |
| 2008/0275477 A1 | 11/2008 | Sterrett | |
| 2008/0287951 A1 | 11/2008 | Stoneburner | |
| 2008/0306553 A1 | 12/2008 | Zucherman | |
| 2009/0043316 A1 | 2/2009 | Durgin | |
| 2009/0054933 A1 | 2/2009 | Mickiewicz | |
| 2009/0069812 A1 | 3/2009 | Gillard | |
| 2009/0069851 A1 | 3/2009 | Gillard | |
| 2009/0105717 A1 | 4/2009 | Bluechel | |
| 2009/0171402 A1 | 7/2009 | Dell'Oca | |
| 2010/0042106 A1 * | 2/2010 | Bryant | A61B 17/8869 606/103 |
| 2010/0057091 A1 | 3/2010 | Oosterom | |
| 2010/0094294 A1 | 4/2010 | Gillard | |
| 2010/0094362 A1 | 4/2010 | Lutze | |
| 2010/0121387 A1 | 5/2010 | Belliard | |
| 2010/0179595 A1 | 7/2010 | Jackson | |
| 2010/0256612 A1 | 10/2010 | Dell'Oca | |
| 2010/0305571 A1 * | 12/2010 | Pratt | A61B 17/8869 606/74 |
| 2010/0318137 A1 | 12/2010 | Stucki | |
| 2010/0331844 A1 | 12/2010 | Ellis | |
| 2010/0331892 A1 | 12/2010 | Fell | |
| 2011/0079315 A1 | 4/2011 | Norton | |
| 2011/0112537 A1 * | 5/2011 | Bernstein | A61B 17/8869 606/74 |
| 2011/0218580 A1 | 9/2011 | Schwager | |
| 2011/0224676 A1 | 9/2011 | Dell'Oca | |
| 2011/0319978 A1 | 12/2011 | Schaffer | |
| 2012/0016384 A1 | 1/2012 | Wilke | |
| 2012/0089193 A1 | 4/2012 | Stone | |
| 2012/0215224 A1 * | 8/2012 | Songer | A61B 17/82 606/74 |
| 2012/0226321 A1 | 9/2012 | Gonzalez-Hernandez | |
| 2012/0303065 A1 | 11/2012 | Larroque-Lahitette | |
| 2013/0116736 A1 * | 5/2013 | De Oliveira | A61B 17/0467 606/86 R |
| 2013/0165933 A1 * | 6/2013 | Gephart | A61B 17/8076 606/70 |
| 2013/0167334 A1 * | 7/2013 | Gephart | A61B 17/8861 24/69 R |
| 2013/0289564 A1 | 10/2013 | Bernstein | |
| 2013/0331897 A1 | 12/2013 | Holt | |
| 2014/0058445 A1 | 2/2014 | Mattchen | |
| 2014/0088688 A1 | 3/2014 | Lilburn | |
| 2014/0142638 A1 * | 5/2014 | Goodwin | A61B 17/842 606/281 |
| 2015/0038969 A1 | 2/2015 | Garcia | |
| 2015/0127003 A1 * | 5/2015 | Songer | A61B 17/8894 606/74 |
| 2015/0182674 A1 | 7/2015 | Schaffer | |
| 2015/0209096 A1 * | 7/2015 | Gephart | A61B 17/842 606/74 |

(56) References Cited

U.S. PATENT DOCUMENTS

| | | | |
|---|---|---|---|
| 2015/0313656 A1* | 11/2015 | Hulliger | A61B 17/823 606/74 |
| 2015/0342654 A1* | 12/2015 | Gephart | A61B 17/8869 606/74 |
| 2016/0174997 A1 | 6/2016 | Spitznagel | |
| 2016/0331431 A1* | 11/2016 | Gephart | A61B 17/8076 |
| 2017/0071648 A1 | 3/2017 | Dell'Oca | |
| 2017/0143394 A1* | 5/2017 | Goodwin | A61B 17/842 |
| 2017/0156779 A1* | 6/2017 | Bryant | A61B 17/8869 |
| 2017/0209190 A1 | 7/2017 | Goodwin | |
| 2018/0029824 A1* | 2/2018 | Gephart | B65H 59/20 |
| 2019/0015142 A1 | 1/2019 | Mitchell | |

FOREIGN PATENT DOCUMENTS

| | | |
|---|---|---|
| DE | 7707950 U | 4/1978 |
| TW | 314764 | 9/1997 |
| WO | 9400063 | 1/1994 |
| WO | 9428812 | 12/1994 |
| WO | 0149191 | 7/2001 |
| WO | 0234120 | 5/2002 |
| WO | 2006088452 | 8/2006 |
| WO | 2011041624 | 4/2011 |
| WO | 2011116364 | 9/2011 |
| WO | 2013003719 | 1/2013 |
| WO | 2014140100 | 9/2014 |
| WO | 2017127692 | 7/2017 |

OTHER PUBLICATIONS

U.S. Appl. No. 62/368,753, filed Jul. 29, 2016, Matthew P. Gephart.

Acute Innovation—Quick and Easy Installation & Re-entry, Acute Innovation, LLC, htto://www.acuteinnovations.com/oroducts/AcuTie/Installtion, May 16, 2012, 7 pages.

Ease of Wire with the Stability of a Plate, AcuTie Sternal Closure System, Oct. 2010, 12 pages.

International Search Report and Written Opinion of International Patent Application No. PCT/US2017/041364, dated Sep. 29, 2017, 6 pages.

Re-Entry Options, AcuTie Sternal Closure System, accessed May 16, 2012, 1 page.

SternaLock Blu Primary Closure System, Biomet Microfixation, Form No. BMF00-3265, Rev 05k1110, 2011, 10 pages.

Technique Guide, Modular Sternal Cable System Flexibility and Strength in Sternal Closure and Repair, Synthes CMF, Jul. 2008, 39 pages.

Technique Guide, Titanium Sternal Fixation System for Stable Internal Fixation of the Sternum, Synthes, Inc., Oct. 2010, 36 pages.

* cited by examiner

SURGICAL CABLE TENSIONER

CROSS-REFERENCE TO RELATED APPLICATION

This application claims the benefit of U.S. Provisional Patent Application No. 62/368,753, filed Jul. 29, 2016, which is hereby incorporated by reference in its entirety.

FIELD

This disclosure relates to surgical instruments and, more particularly, to instruments for tensioning surgical cables.

BACKGROUND

Cable tensioners may be used to apply tension to a surgical cable. In one approach, the surgical cable has one end attached to a locking device, such as a crimp, and another end which is looped around a bone, advanced through the crimp, and advanced through a cable tensioner. To tension the surgical cable, a distal end of the cable tensioner is positioned against the crimp and a tensioning mechanism of the cable tensioner is operated to tension the surgical cable. Once the desired tension has been applied to the surgical cable, the crimp is fixed to the cable to hold the applied tension in the cable and secure the tensioned cable around the bone.

Some cable tensioners have complicated tensioning mechanisms with many components. The components can include for example a device to grip the surgical cable, a linkage to shift the cable away from the distal end of the cable tensioner and tension the surgical cable, a ratchet to resist movement of the device back toward the cable tensioner distal end, and a tension gauge. These more complicated tensioning mechanisms may render the cable tensioner unsuitable for being disposable from a cost perspective.

Another problem with some cable tensioners is that the cable tensioners have a ratchet for resisting loss of tension in the cable during a tensioning operation. The ratchet may include a pawl that engages recesses of a rack. However, as the pawl shifts out of recesses of the rack during a tensioning operation, the rack could shift backward before the pawl engages one of the recesses and cause a loss of tension in the cable.

SUMMARY

In accordance with one aspect of the present disclosure, an instrument for tensioning a surgical cable is provided that includes a rotary tensioner that is rotatable in a tensioning rotary direction to apply tension to the surgical cable. The instrument further includes a body supporting the rotary tensioner, a pawl portion of the body configured to be received at least partially in one of the recesses of the ratchet gear, and a living hinge portion of the body supporting the pawl portion. The living hinge portion is configured to permit the pawl portion to be shifted out of the one recess and shifted into an adjacent one of the recesses of the ratchet gear with turning of the tensioner in the tensioning rotary direction. Because the pawl portion of the body is supported by the living hinge portion of the body, a separate spring for biasing the pawl portion and a separate structure for guiding the pawl portion are not required which simplifies manufacture and use of the instrument.

In one form, the instrument further includes a second living hinge portion of the body and a second pawl portion configured to be received at least partially in another recess of the ratchet gear. The second living hinge portion is configured to permit the second pawl portion to be shifted out of the recess and at least partially into an adjacent recess of the ratchet gear with turning of the rotary tensioner in the rotary tension direction. The pawl portions and living hinge portions may be configured so that one of the pawl portions is always received at least partially in one of the recesses of the rotary tensioner ratchet gear to resist turning of the rotary tensioner in a pay out rotary direction. In this manner, the pawl portion received at least partially in the one recess resists turning of the rotary tensioner in the pay out rotary direction during a tensioning procedure to inhibit loss of tension in the surgical cable during the tensioning procedure.

In accordance with another aspect of the present disclosure, an instrument for tensioning a surgical cable is provided including a one piece body having a cavity and a rotary tensioner at least partially in the cavity. The rotary tensioner is rotatable relative to the body in a tensioning rotary direction to wind a surgical cable onto the rotary tensioner. The instrument further includes ratchet portions of the one-piece body and the rotary tensioner configured to permit the rotary tensioner to turn in the tensioning rotary direction and resist turning of the rotary tensioner in an opposite, pay out rotary direction. In this manner, the one-piece body both supports the rotary tensioner and includes a ratchet portion that resists turning of the rotary tensioner. This allows the instrument to be made from fewer components. In one approach, the one-piece body and rotary tensioner are made from a plastic material that allows the instrument to be discarded or recycled after use.

DETAILED DESCRIPTION

Figure 1:
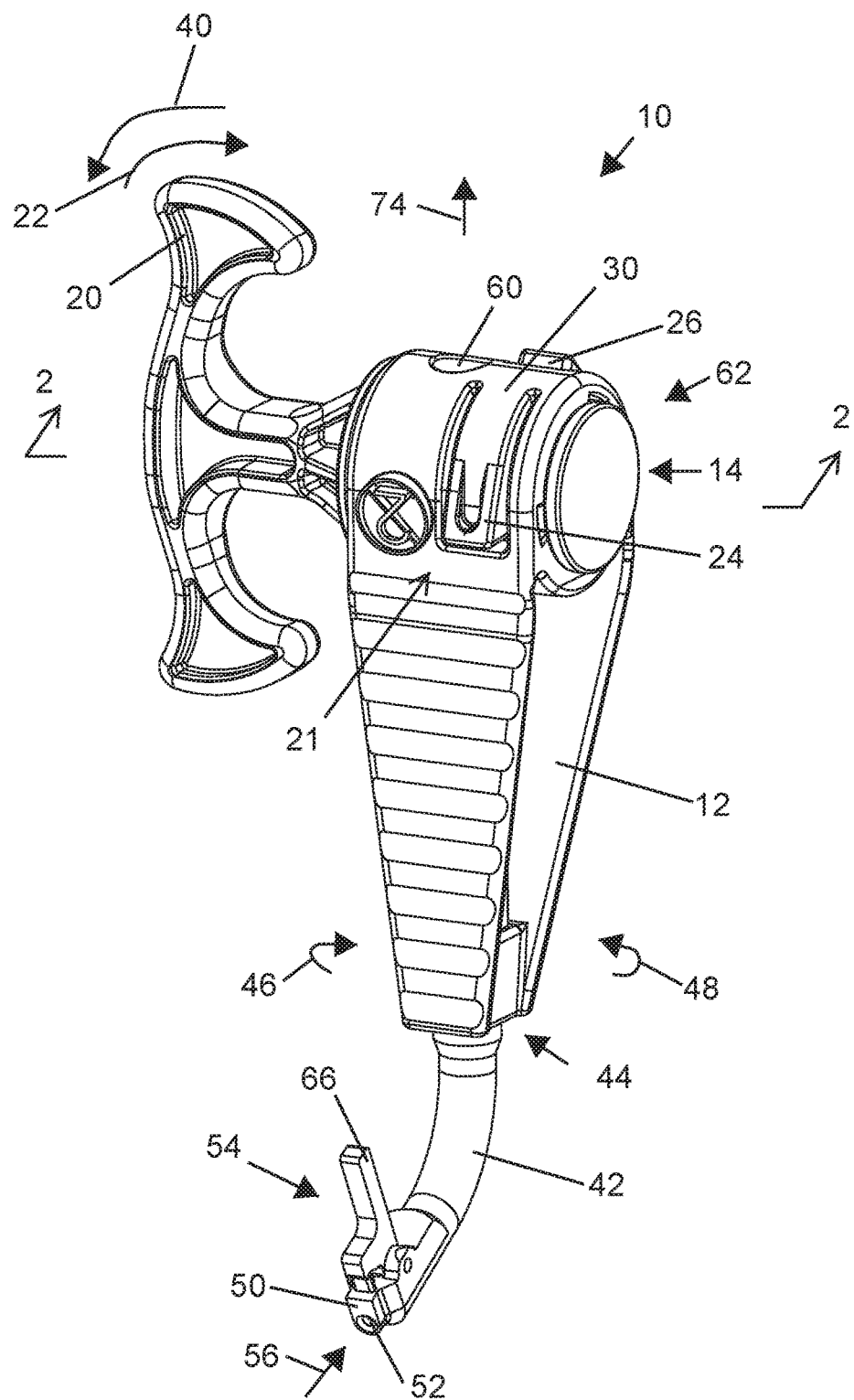
FIG. 1 is a perspective view of a cable tensioner showing a body of the cable tensioner having a living hinge that supports a first pawl of the cable tensioner.
Figure 2:
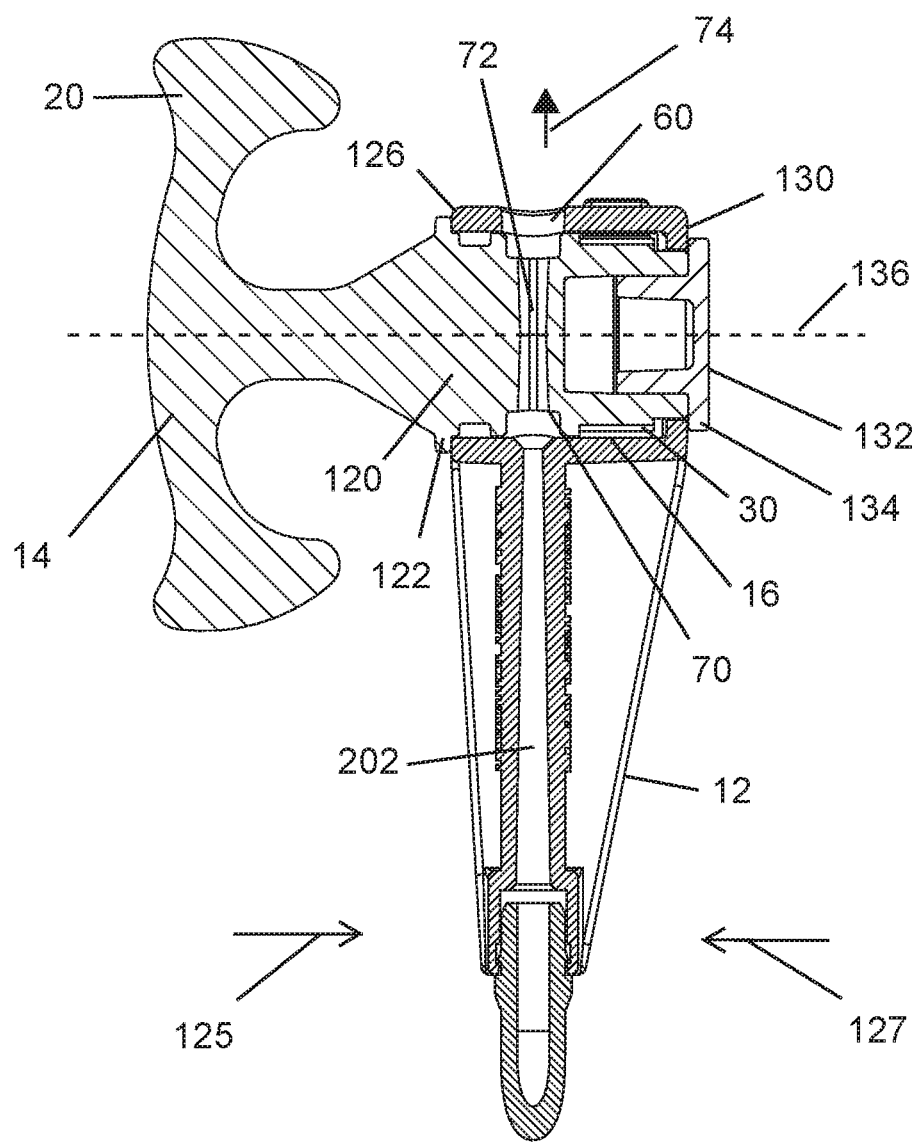
FIG. 2 is a cross-sectional view taken across line 2-2 in FIG. 1 showing a rotary tensioner of the cable tensioner supported in a cavity of the body.

With reference to FIGS. 1 and 2, a cable tensioner 10 is provided having a body 12 and a rotary tensioner 14 rotatably supported in a cavity 16 of the body 12. The rotary tensioner 14 includes a handle 20 for turning the rotary tensioner 14 in a tensioning rotary direction 22 and applying tension to a surgical cable 23. The cable tensioner 10 has a guide, such as a tube 42, a distal end 50 that includes an opening 52, and a cutting tool 54. To apply tension to the cable 23, the surgical cable 23 is advanced in direction 56 through the opening 52, through the cable tensioner 10, and outward from an opening 60 of the body 12. The cable tensioner 10 is advanced along the surgical cable 23 until the distal end 50 abuts a crimp, bone plate, or other locking device for securing the surgical cable 23 once the surgical cable 23 has been tensioned. For example with reference to FIG. 10, the distal end 50 may abut a crimp 212 and the surgical cable 23 extends through the cable tensioner 10.

Returning to FIG. 1, the handle 20 is then turned in tensioning rotary direction 22 to draw the cable 23 onto the rotary tensioner 14 and apply tension to the cable 23 as discussed in greater detail below. The surgeon uses tactile feedback from the handle 20 to determine the tension in the surgical cable 23. Once the desired tension has been applied to the cable 23, the crimp 212 is reconfigured to secure the cable 23. Next, the surgeon manipulates an actuator of the cutting tool 54, such as a lever 66, to cut the cable 23. The cable tensioner 10 and the cable 23 therein may then be removed from the surgical site.

Figure 8:
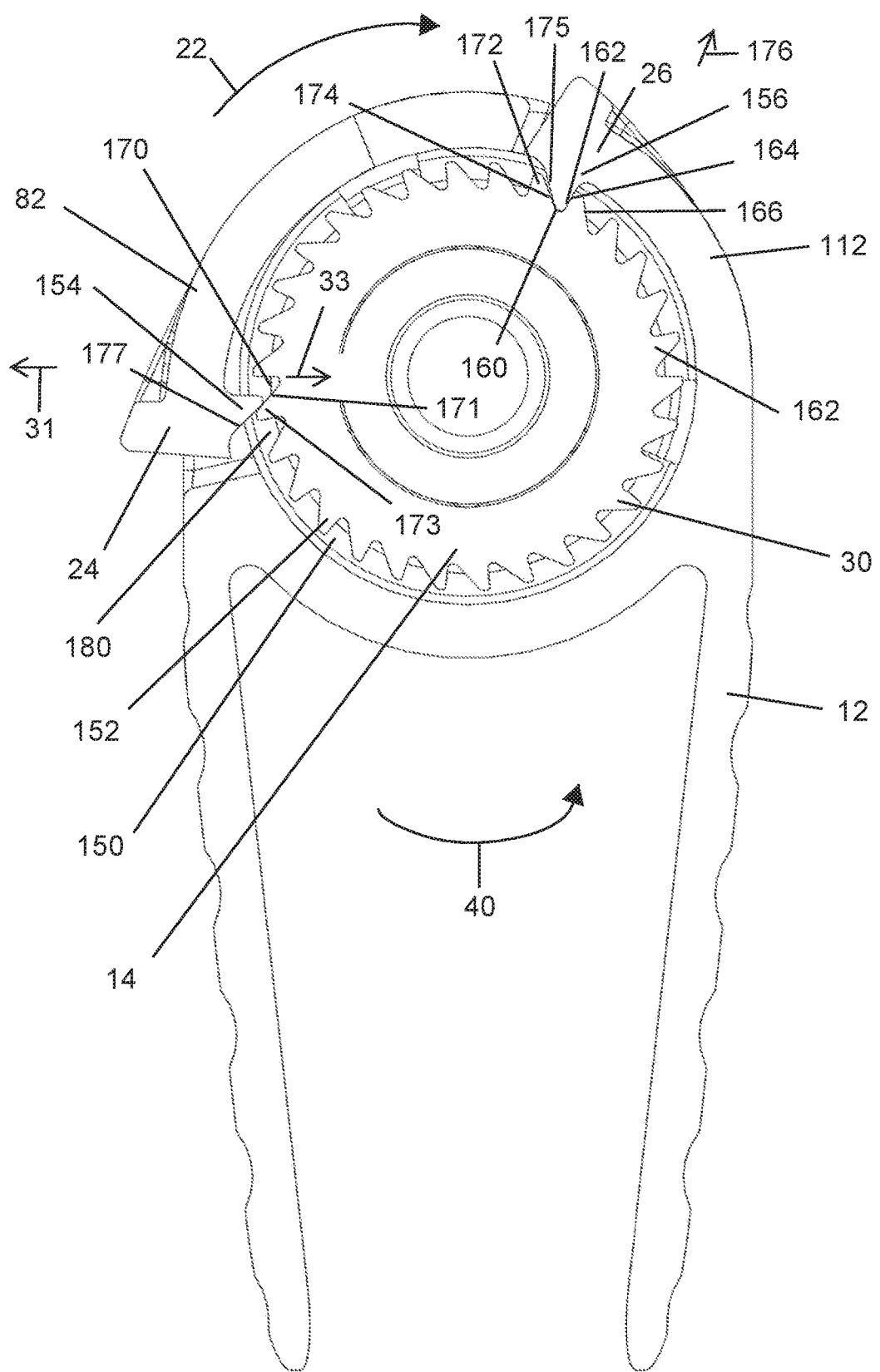
FIG. 8 is a cross-sectional view taken across line 8-8 in FIG. 5 showing the second pawl engaged in a first recess of the ratchet gear and the first pawl shifted out of engagement from a second recess of the ratchet gear.

The body 12 has a ratchet mechanism 21 for resisting turning of the rotary tensioner 14 in a pay out rotary direction 40, which would pay the cable 23 off of the rotary tensioner 14. The ratchet mechanism 21 includes at least one pawl or pawl portion, such as a pair of pawls or pawl portions 24, 26, which engage a ratchet gear 30 of the rotary tensioner 14, as shown in FIG. 8. The pawl portions 24, 26 have projections 154, 156 that engage recesses 150 of the ratchet gear 30 between teeth 152 of the ratchet gear 30.

Figure 6:
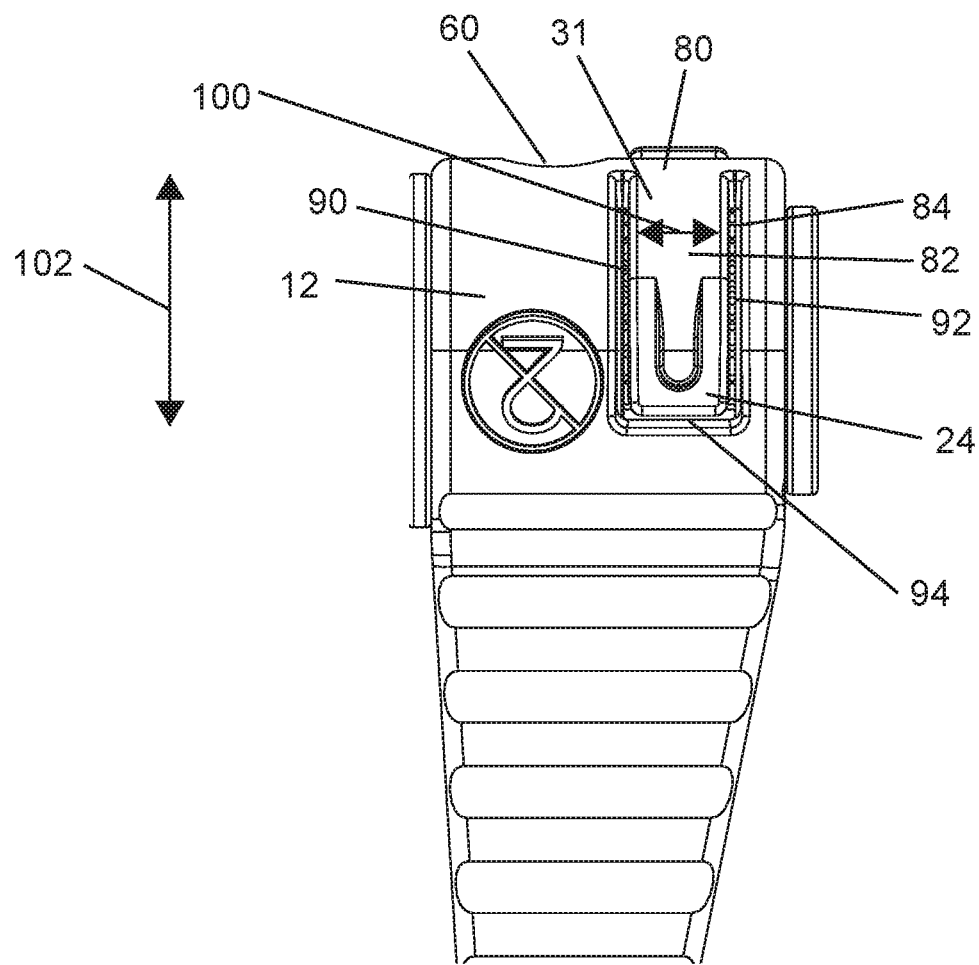
FIG. 6 is a front elevational view of a portion of the body of the cable tensioner of FIG. 1 showing a generally u-shaped through opening in the body defining an outer periphery of the first pawl and the living hinge.
Figure 7:
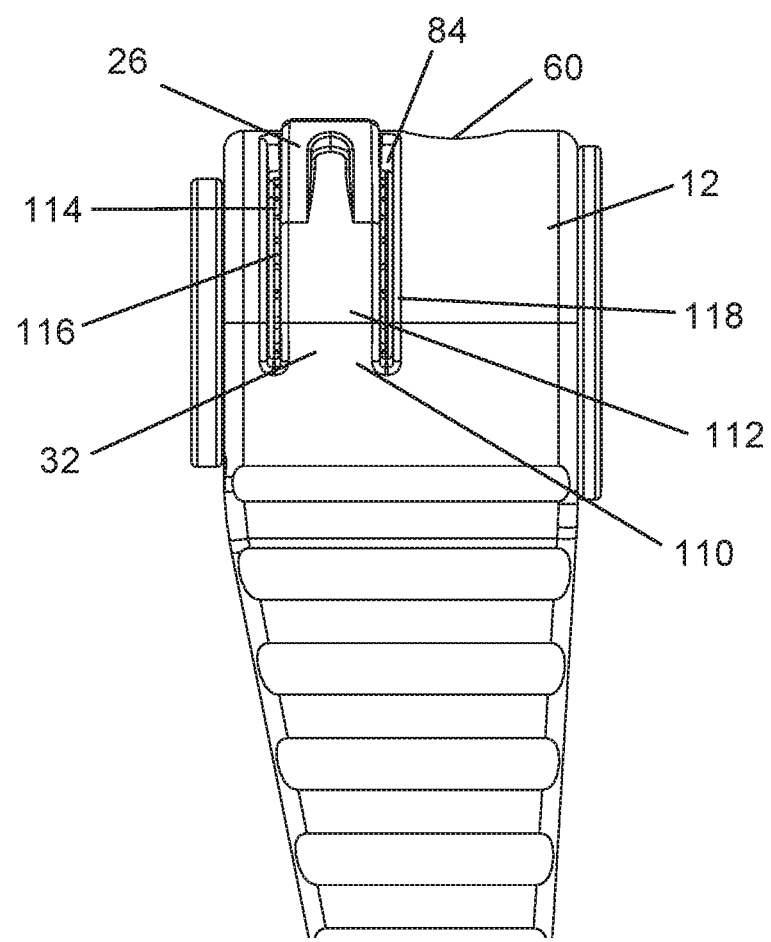
FIG. 7 is a rear elevational view of a portion of the body of FIG. 6 showing a through opening of the body extending about the second pawl and a living hinge supporting the second pawl.

With reference to FIGS. 1, 6, and 7, the body 12 includes living hinges or living hinge portions 31, 32 that permit the pawl portions 24, 26 to shift radially outward and inward in directions 31, 33 (see FIG. 8) and travel over teeth 152 of the ratchet gear 30 as the rotary tensioner 14 is turned in the tensioning rotary direction 22. The living hinge portions 31, 32 and the pawl portions 24, 26 should be understood to include both living hinges that are originally integrally formed with the body 12 or are initially formed as separate components that are later unified or securely connected to the body 12 after they are formed, as will be described more fully hereinafter.

The living hinge portions 31, 32 are resiliently flexible to permit shifting of the pawl portions 24, 26 when the rotary tensioner 14 is turned in the tensioning rotary direction 22 while being sufficiently strong to support to the pawl portions 24, 26 when the pawl portions 24, 26 are engaged in the recesses 150 of the rotary tensioner 14 and resist turning of the rotary tensioner 14 in the tensioning rotary direction 22.

Figure 9:
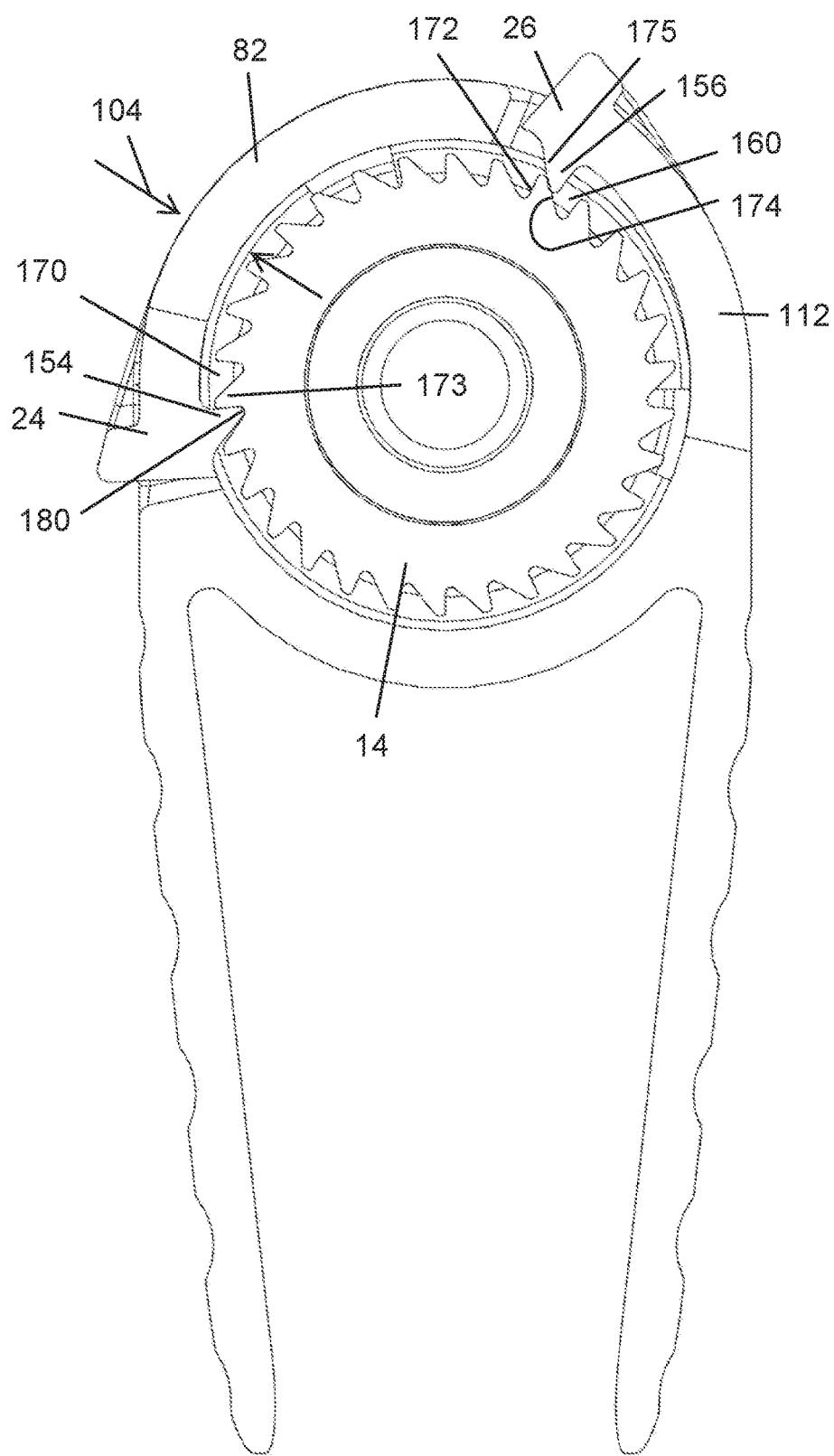
FIG. 9 is a cross-sectional view similar to FIG. 8 showing the rotary tensioner turned in a tensioning rotary direction so that the second pawl is shifted out of engagement with the first recess and the first pawl shifted into engagement in a third recess of the ratchet gear.

With reference to FIG. 8, the pawl portions 24, 26 are spaced circumferentially around the rotary tensioner 14 so that the pawl portions 24, 26 engage the ratchet gear 30 at different positions around the ratchet gear 30. The pair of pawl portions 24, 26 and the living hinge portions 31, 32 are configured so that one of the pawl portions 24, 26 is always engaged in one of the recesses 150 of the ratchet gear 30 when a user is turning the handle 20 in the tensioning rotary direction 22. For example, when the pawl portion 24 is shifting out of the recess 170 as shown in FIG. 8, the pawl portion 26 is engaged with the recess 160. Conversely, when the pawl portion 26 is shifting out of the recess 160 as shown in FIG. 9, the pawl portion 24 is engaged in the recess 180. Because one of the pawl portions 24, 26 is always engaged with the ratchet gear 30, the one of the pawl portions 24, 26 can resist turning of the rotary tensioner 14 in the pay out rotary direction 40 and maintain tension in the cable 23 during a tensioning operation.

In one form, the body 12 and the rotary tensioner 14 may each have a one-piece construction which simplifies manufacture and assembly of these components. As used herein, the term one-piece refers to a monolithic member. For example, the body 12 including the living hinge portions 31, 32 and the pawl portions 24, 26 has a one-piece construction and may be formed by, for example, molding, 3D printing, or machining. Likewise, the rotary tensioner 14 including the handle 20 may have a one-piece construction such as by molding, 3D printing, or machining. This simplifies manufacture by reducing the overall number of components of the cable tensioner 10.

Further, the body 12 and the rotary tensioner 14 may be made from the same or different materials, such as a plastic or a composite material to reduce the weight of the cable tensioner 10 and make the cable tensioner 10 easier to handle. For example, the body 12 and the rotary tensioner 14 may be made from RADEL® plastic. In other forms, the body 12 and the rotary tensioner 14 may made from other plastics. The materials for the rotary tensioner 14 may be selected so that the teeth 152 are able to withstand 80-100 pounds of force during a cable tensioning operation. The materials of the cable tensioner 10 may be selected so that the cable tensioner 10 is disposable or recyclable. In other forms, the materials of the cable tensioner 10 may be selected to permit cleaning and reuse of the cable tensioner 10. For example, the body 12 and the rotary tensioner 14 may be made from a metallic material, such as stainless steel.

In other forms, the body 12 and the rotary tensioner 14 may each be made from a plurality of components. For example, the body 12 may include the living hinge portions 31, 32 and the pawl portions 24, 26 may be initially formed as separate components that are thereafter joined such as by chemical welding or adhesive to the living hinge portions 31, 32. The rotary tensioner 14 could likewise be initially formed by separate components such as a handle 20 and ratchet gear 30 that are later fixed together for assembly using fasteners.

With respect to FIG. 1, the tube 42 of the cable tensioner 10 is connected to the body 12 at a swivel connection 44.

The swivel connection 44 permits the body 12 to turn in opposite directions 46, 48 relative to the tube 42. This allows the user to adjust the position of the body 12 and handle 23 to an ergonomically comfortable position during a cable tensioning operation while the distal end 50 abuts the crimp 212.

Figure 3:
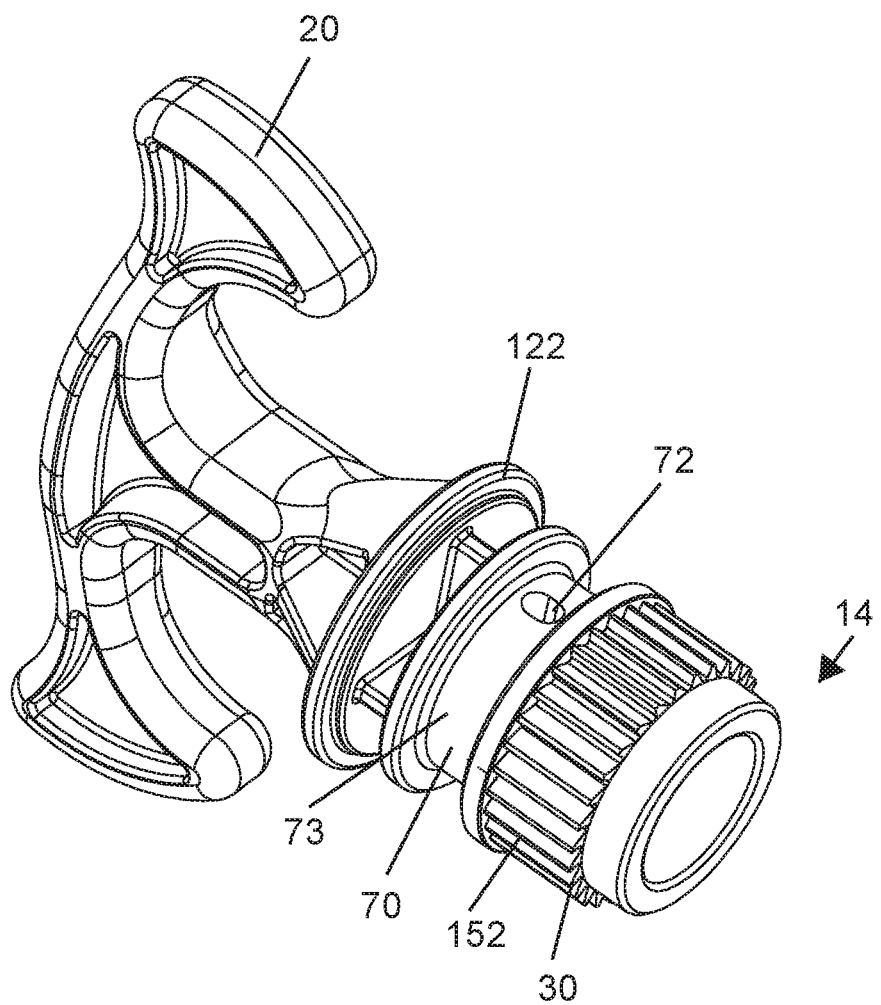
FIG. 3 is a perspective view of the rotary tensioner of FIG. 2 showing a drum portion for wrapping the surgical cable thereon and a ratchet gear of the rotary tensioner.
Figure 10:
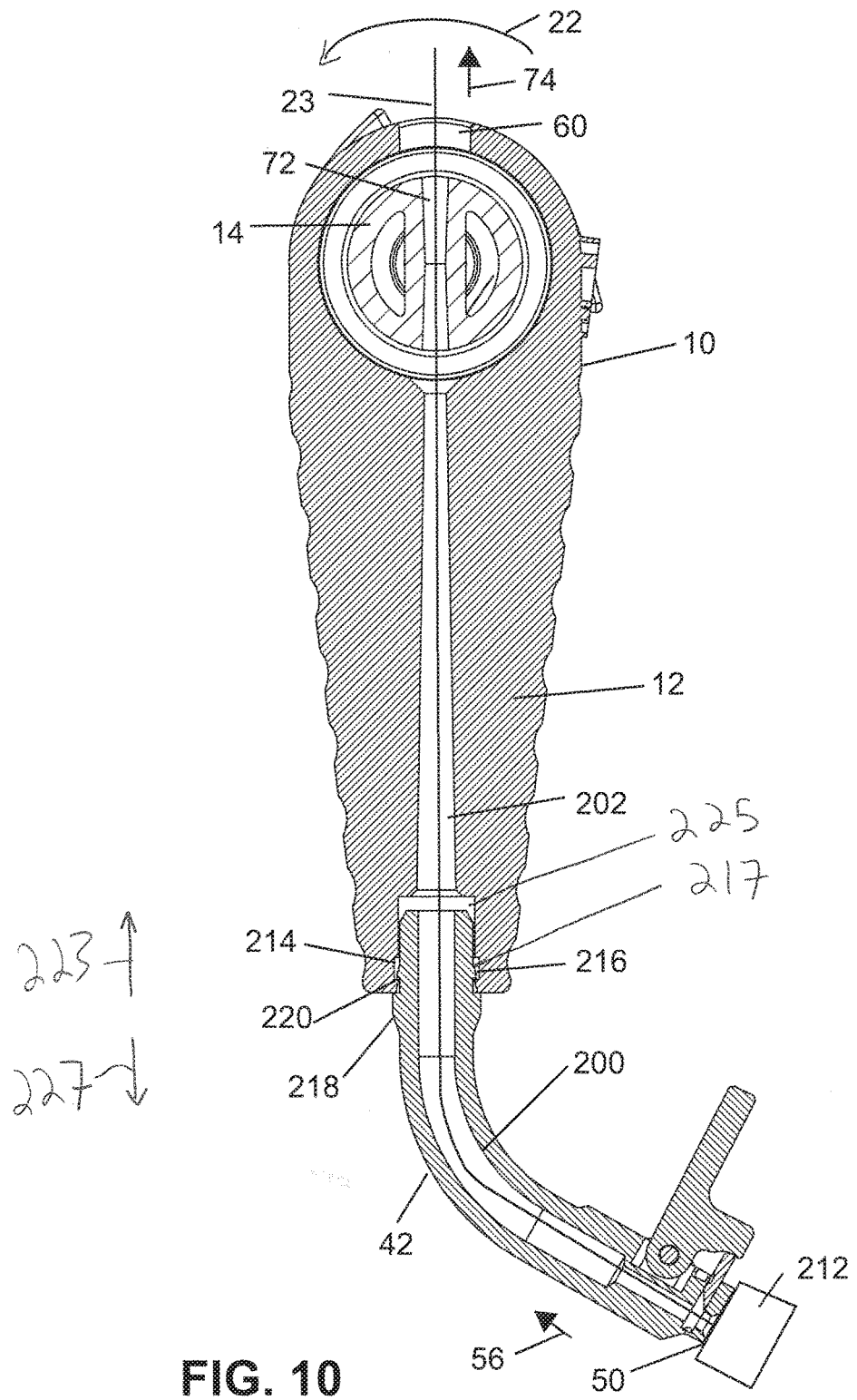
FIG. 10 is a cross-sectional view taken across line 10-10 in FIG. 5 showing a distal end of the cable tensioner abutting a crimp and a surgical cable extending outward from the crimp and through passages of a guide tube of the cable tensioner, the body of the cable tensioner, and the rotary tensioner of the cable tensioner.
Figure 11:
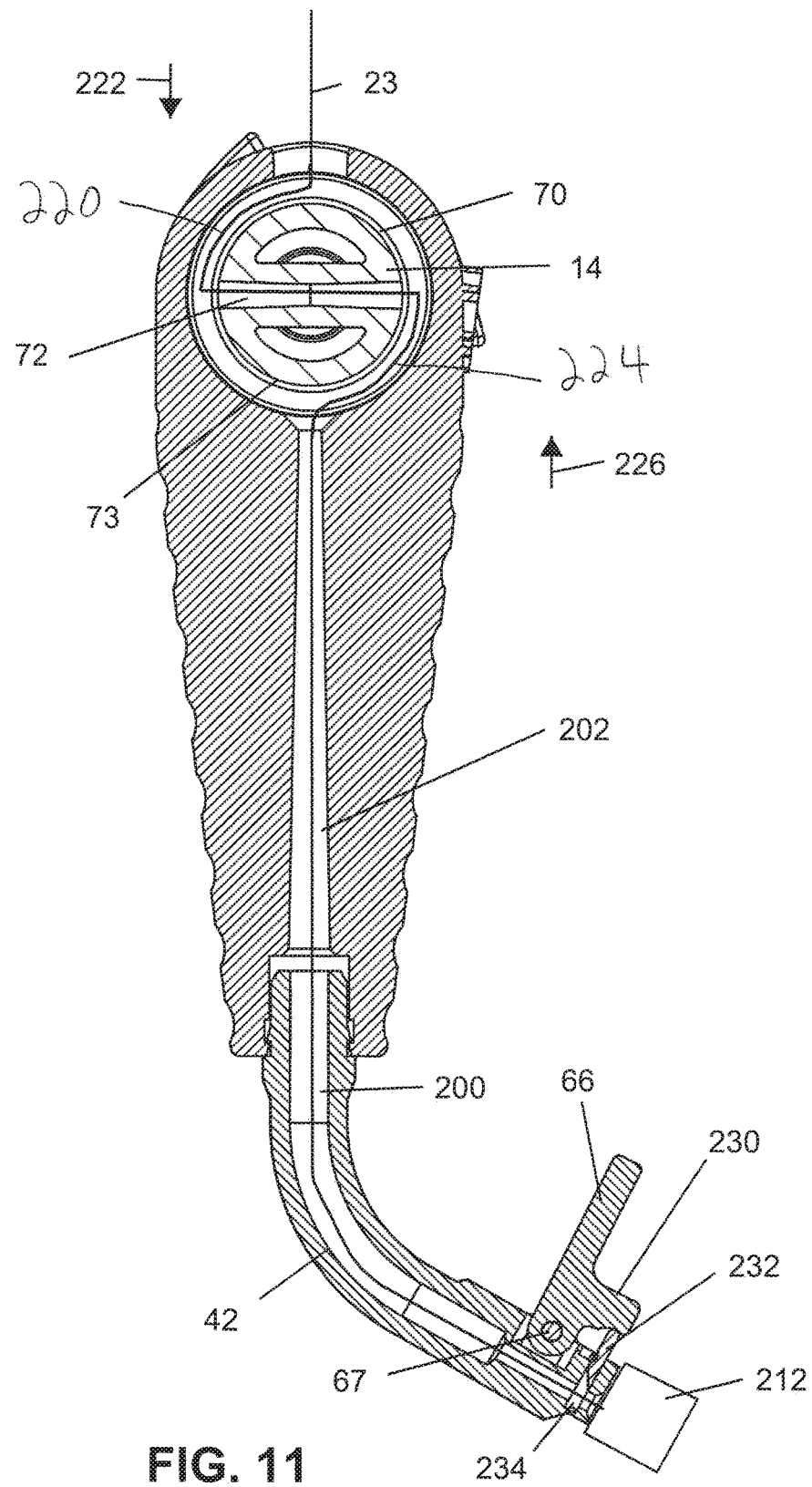
FIG. 11 is a cross-sectional view similar to FIG. 10 showing the rotary tensioner turned in the tensioning rotary direction from its position in FIG. 10 which draws the cable onto the drum portion of the rotary tensioner and tensions the cable.

With reference to FIGS. 2 and 3, the rotary tensioner 14 has a drum portion 70 with a passage 72 extending therethrough and a cylindrical outer surface 73. When the handle 20 is in the vertical orientation shown in FIG. 2, the passage 72 of the drum portion 70 is aligned with the opening 60 of the body 12 and a passage 202 of the body 12. The cable 23 may be advanced in direction 74 upward through the passages 72, 202 and out from the opening 60 (see FIG. 10). When the handle 20 is turned in the tensioning rotary direction 22, the drum portion 70 and passage 72 turn with the handle 20 and wind the cable 23 onto the cylindrical outer surface 73 of the drum portion 70 as shown in FIGS. 10 and 11.

With reference to FIG. 6, the living hinge portion 31 includes a base portion 80 and an arm portion 82 that connects the base portion 80 and the pawl portion 24. The body 12 has a generally U-shaped through opening 84 extending around the arm portion 82 and the pawl portion 24. The through opening 84 includes straight portions 90, 92, and an end portion 94 connecting the straight portions 90, 92. The arm portion 82 has a width 100, a length 102, and a thickness 104 (see FIG. 9), that are selected with the material of the body 12 to permit sufficient flexibility for the pawl portion 24 to be deflected by the ratchet gear 30 when the handle 20 is turned in the tensioning rotary direction 22. However, the arm portion 82 is sufficiently strong to resist deflecting when the pawl portion 24 is engaged with the ratchet gear 30 and the tension in the cable 23 urges the rotary tensioner 14 in the pay-out rotary direction 40. For example, the arm portion 82 may be configured to resist forces applied by the rotary tensioner 14 in the range of approximately 80 pounds to approximately 100 pounds without deflecting. As another example, the body 12 including the living hinge portion 31 may be made of RADEL® plastic and the arm portion 82 has a width 100 in the range of approximately 0.2 inches to approximately 0.3 inches, such as 0.283 inches, and a thickness 104 (see FIG. 9) in the range of approximately 0.08 inches to approximately 0.12 inches, such as 0.098 inches. The arm portion 82 and the pawl portion 24 may have a length 102 in the range of approximately 0.6 inches to approximately 0.9 inches, such as approximately 0.7 to approximately 0.8 inches, such as approximately 0.77 inches.

As shown in FIG. 7, the living hinge portion 32 is similar to the living hinge portion 31. The living hinge 32 includes a base portion 110 and an arm portion 112. The body includes a generally U-shaped through opening 114 extending about the arm portion 112 and the pawl portion 26. The through opening 114 includes a pair of straight portions 116, 118 and an end portion 120 (see FIG. 4) connecting the straight portions 116, 118.

With continued reference to FIG. 7, the pawl portion 26 has a raised feature on it exterior wherein the raised feature has an upside-down U-shape and defines a recess. In the event the cable tensioner 10 must be removed from the cable 23 after tensioning the cable 23, but the cable 23 cannot be cut, a surgeon may grab the raised feature with forceps and lift the pawl portion 26 out of engagement with the ratchet gear 30. The surgeon would perform a similar procedure on the pawl portion 24 so that both pawl portions 24, 26 are disengaged from the ratchet gear 30. With the pawl portions 24, 26 disengaged from the ratchet gear 30, the handle 20 may be turned in the pay out rotary direction 44 to pay the cable 23 off of the drum portion 70. Although the raised features of the pawl portions 24, 26 allow a surgeon to pay out the cable 23 from the cable tensioner 10 when the cable 23 cannot be cut, in normal procedures, the cable 23 will simply be cut and removed with the cable tensioner 10 such that paying out the cable 23 from the drum portion 70 is unnecessary.

Returning to FIGS. 2 and 3, the rotary tensioner 14 has a body 120 that includes the drum portion 70. The body 120 has a retention flange 122 for contacting a rim 126 of the body 12 extending about the cavity 16. The contact between the flange 122 and the rim 126 limits movement of the rotary tensioner 14 in direction 125 along an axis 136 of rotation of the rotary tensioner 14. The body 12 also has an inwardly directed lip 130 extending about the cavity 16. The rotary tensioner 14 includes a cap 132 secured to the body 120, such as by adhesive or a snap-fit. The cap 132 has a flange 134 for contacting the lip 130 of the body 12 and limiting movement of the rotary tensioner 14 in direction 127 along the axis 136. In this manner, the flanges 122, 134 of the rotary tensioner 14 are in axial overlapping relation with the rim 126 and the lip 130 of the body 12. This captures the rotary tensioner 14 within the cavity 16 of the body 12.

Figure 4:
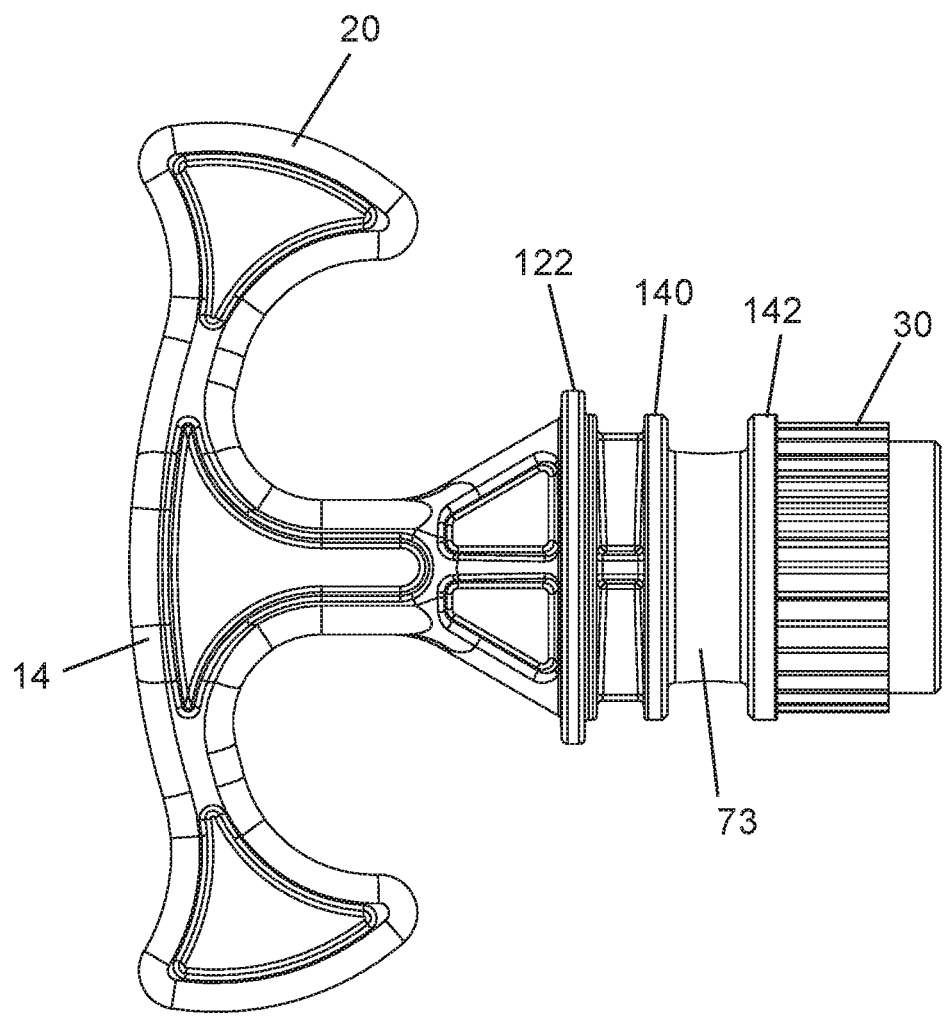
FIG. 4 is an elevational view of the rotary tensioner of FIG. 3 showing a handle of the rotary tensioner connected to the drum portion and the ratchet gear.
Figure 5:
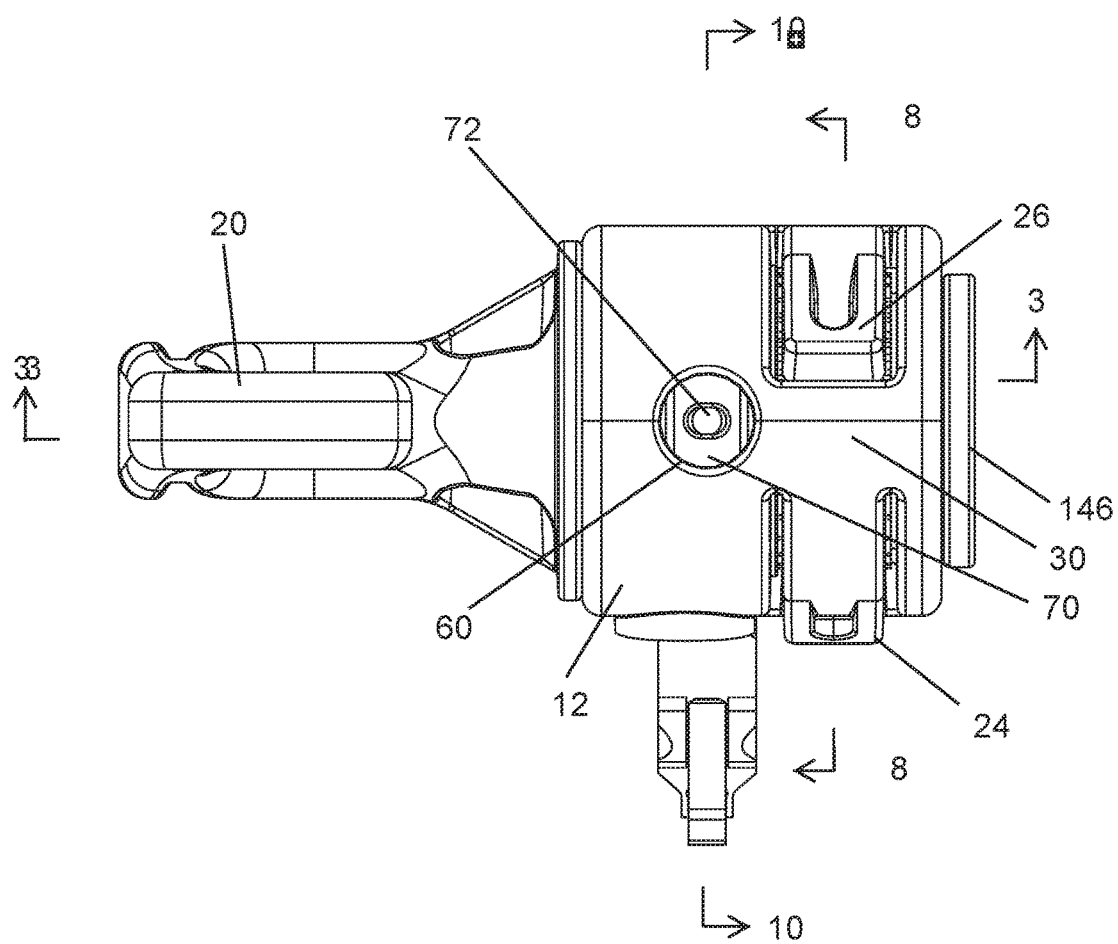
FIG. 5 is a top plan view of the cable tensioner of FIG. 1 showing the first pawl on the front of the body of the cable tensioner and a second pawl on the rear of the body.

With reference to FIG. 4, the rotary tensioner 14 also includes guide flanges 140, 142 on opposite sides of the outer cylindrical surface 73 of the drum portion 70. The guide flanges 140, 142 resist lateral movement of the cable 23 off of the drum portion 70 as the cable 23 is wound up on the outer cylindrical surface 73.

Turning to FIG. 8, the operation of the pawl portions 24, 26 and the ratchet gear 30 as the rotary tensioner 14 is turned in the tensioning rotary direction 22 to tension the surgical cable 23 will be discussed in greater detail. The pawl portions 24, 26 include projections 154, 156 that are received in different recesses 150 around the ratchet gear 30, such as at approximately the nine o'clock and the one o'clock positions as shown in FIG. 8. Initially, the projection 156 is fully engaged in the recess 160 and has a stop surface 162 abutting a stop surface 164 of a tooth 166 of the ratchet gear 30. Due to the abutting stop surfaces 164, 166, the rotary tensioner 14 is held against rotation in the pay out rotary direction 40.

In FIG. 8, the pawl portion 24 is shown with the projection 154 urged radially outward in direction 31 from a recess 170 of the ratchet gear 30 via camming engagement between a ramp surface 177 of the projection 154 and a ramp surface 171 of a tooth 173. Thus, while the projection 156 of the pawl portion 26 is fully engaged in the recess 160, the projection 154 of the pawl portion 24 is shifted out of engagement from the recess 170 as shown in FIG. 8. The pawl portion 26 thereby resists turning of the rotary tensioner 14 in the pay-out rotary direction 40 while the pawl portion 24 shifts radially outwardly in direction 31 and travels over the tooth 173.

The ratchet gear 30 has a tooth 172 with a ramp surface 174 facing a ramp surface 175 of the projection 156. When the rotary tensioner 14 is turned in the tensioning rotary direction 22, the ramp surfaces 174, 175 cammingly engage and cause the pawl portion 26 to shift radially outward in direction 176 which flexes the living hinge 32 to a deflected configuration. Turning to FIG. 9, the rotary tensioner 14 has been turned in the tensioning rotary direction 22 such that the caroming engagement between the ramp surfaces 174, 175 have urged the projection 156 radially outwardly in direction 176 out of engagement with the recess 160 and flexed the living hinge portion 31 to the deflected configuration. The rotation of the rotary tensioner 14 in the tensioning rotary direction 22, however, has rotated the ratchet gear 30 until the projection 154 is aligned with a recess 180 of the ratchet gear 30 on an opposite side of the tooth 173 from the recess 170. The living hinge portion 31 resiliently urges the projection 154 radially inward in direction 33 into the recess 180 and engages the projection 154 with the recess 180. In this manner, the living hinge portion 31 flexes to back to a generally undeflected configuration. The term undeflected configuration is used to compare the configuration of the living hinge portion 31 in FIG. 9 with the deflected configuration of the living hinge portion 31 in FIG. 8. In the undeflected configuration, the material of the living hinge portion 31 may be slightly deflected due to the presence of the rotary tensioner 14 and this partial deflection biases the projection 154 into engagement with the recess 180.

Moving between FIGS. 8 and 9, the projection 156 has been urged outward from the recess 160, while the projection 154 has snapped into and is fully seated within the recess 180. In this manner, at least one of the projections 156, 154 is always fully seated within one of the recesses 150. This provide a precise ratcheting action while utilizing larger teeth 152, which may be more durable than utilizing a single pawl and a ratchet gear with smaller teeth. For example, if the surgeon were to release the handle 20 during a tensioning operation, the rotary tensioner 14 would not turn in the pay out rotary direction 40 from its position in FIG. 9 despite the projection 156 of the pawl portion 26 having been urged radially outward from the recess 160. If the pawl portion 24 were not present, the rotary tensioner 14 could turn in the pay out rotary direction 40 and release tension in the cable 23 until the projection 156 snaps into the recess 160 and the stop surface 162 of the projection 156 abuts the stop surface 164 of the tooth 166. Because one of the pawl portions 24, 26 is always engaged with one of the recesses 150, the release of tension is avoided.

With reference to FIG. 10, the tube 42 includes a tube passage 200 that is aligned with the passage 202 of the body 12. When the handle 20 is in an upright or vertical orientation (see FIG. 1), the tensioner passage 72 is also aligned with the body passage 202 such that the cable 23 may be advanced from the crimp 212 and through the aligned tube passage 200, body passage 202, and tensioner passage 72 before exiting the opening 60 in direction 74.

The swivel connection 44 between the body 12 and the tube 42 includes a groove 214 and a collar 220 of the body 12. The swivel connection 44 further includes a protrusion 216 of the tube 42 that snaps into the groove 214 and a shoulder 218 of the tube 42 below the collar 220. In this manner, the collar 220 of the body is positioned between the protrusion 216 and the shoulder 218 of the tube 42 which rotatably captures the tube 42 on the body 12. In one form, the protrusion 216 has an annular barb shape including a tapered surface 217. During assembly of the cable tensioner 10, the tube 42 is advanced in direction 223 into a socket 225 of the body 12. The tapered surface 217 cams and expands the collar 220 radially outward so that the protrusion of the tube 42 can snap into the groove 214. The protrusion 216 may also have a flat lower surface abutting a flat upper surface of the collar 220 to resist removal of the tube 42 in direction 227 from the socket 225 of the body 12.

Figure 12:
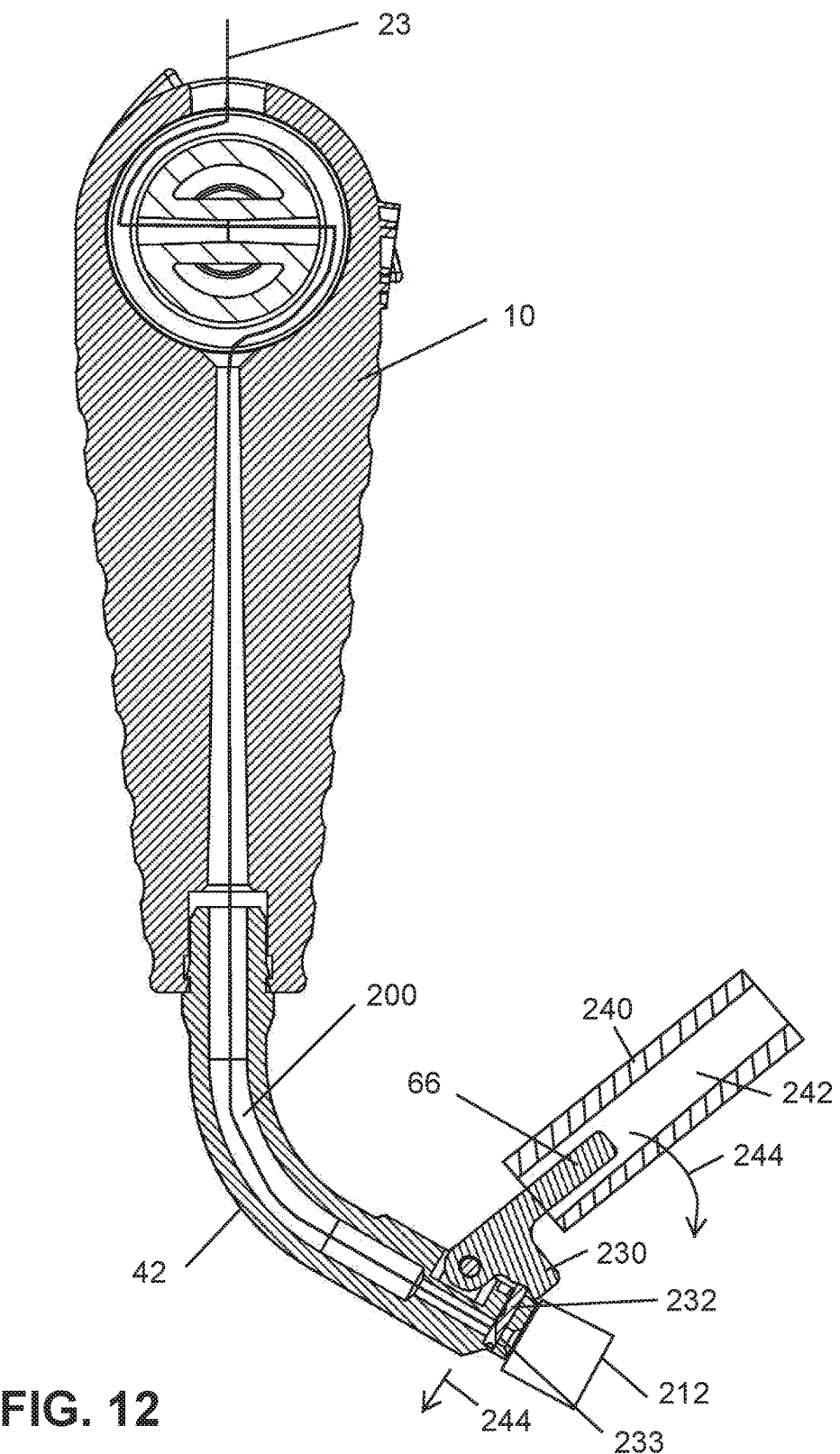
FIG. 12 is a cross-sectional view similar to FIG. 11 showing a lever of a cutting tool of the cable tensioner pivoted by a tubular tool connected to the lever which shifts a cutting blade of the cutting tool and cuts the surgical cable.

As shown in FIGS. 11 and 12, the cutting tool 54 includes a lever 66 pivotally connected to the tube 42 by a pin 67 and a blade 232 slidably received in a slot 234 of the tube 42. The blade 232 has a cutting edge 233 made of a sufficiently strong material to cut the surgical cable 23 The lever 66 has an arm 230 abutting the blade 232. The lever 66 can be pivoted to shift the blade 232 in direction 244 to cut the cable 23 extending through the tube passage 200. In one form, the blade 232 is made of 465 series stainless steel and the lever 66 is also made of stainless steel.

With reference to FIGS. 10-12 a method of tensioning and cutting the cable 23 is shown. Initially, the surgical cable 23 is advanced through the tube passage 200, the body passage 202, and the tensioner passage 72, and outward through the opening 60 in direction 74. The cable tensioner 10 may be advanced along the surgical cable 23 until the distal end 50 abuts against the crimp 212.

Next, the surgeon turns the handle 20 in the tensioning rotary direction 22 which causes the rotary tensioner 14 to turn in the tensioning rotary direction 22 as shown in FIG. 11. The turning of the rotary tensioner 14 in the tensioning rotary direction 22 draws a portion 220 of the cable 23 downward in direction 222 onto the drum portion 70 and draws a portion 224 of the cable 23 upward in direction 226 onto the drum portion 70. As the cable portions 220, 224 are wrapped onto the drum portion 70, tension is applied to the surgical cable 23. The surgeon determines the tension in the surgical cable 23 by way of tactile feedback from the handle 20. As discussed above, the pawl portions 24, 26 engage the ratchet gear 30 to restrict turning of the rotary tensioner 14 in the pay out rotary direction 40 and resist loss of tension in the cable 23. Once the desired tension has been obtained, the crimp 212 or locking device is crimped or otherwise operated to secure the surgical cable 23 at the desired tension.

With reference to FIG. 11, after the crimp 212 has been secured to the cable 23, the surgeon operates the lever 66 to drive the blade 232 and cut the cable 23. In one approach, the surgeon connects a tool to the lever 66 to provide additional leverage to drive the blade 232 and cut the cable 23. For example, a tubular tool 240 may be positioned such that the lever 66 extends into a cannula 242 of the tubular tool 240. The surgeon then pivots the tubular tool 240 and the lever 66 connected therewith in direction 244. This causes the arm 230 to push the blade 232 in direction 244 and cut the cable 23. The cable tensioner 10 and the cable 23 remaining within the cable tensioner 10 may then be removed from the surgical site. Owing to the materials and fewer components of the cable tensioner 10, the cable tensioner 10 may then be discarded or recycled, including being discarded or recycled with the cut section of the cable 23 therein.

While there have been illustrated and described particular embodiments of the present invention, it will be appreciated that numerous changes and modifications will occur to those skilled in the art, and it is intended in the appended claims to cover all those changes and modifications which fall within the true spirit and scope of the present invention.

What is claimed is:

1. An instrument for tensioning a surgical cable, the instrument comprising:
   a rotary tensioner rotatable in a tensioning rotary direction to apply tension to a surgical cable;
   a ratchet gear of the rotary tensioner having a plurality of recesses;
   a body supporting the rotary tensioner;
   a pawl portion of the body configured to be received at least partially in one of the recesses of the ratchet gear; and
   a living hinge portion of the body supporting the pawl portion and configured to permit the pawl portion to be shifted out of the one recess and shifted into an adjacent one of the recesses of the ratchet gear with turning of the rotary tensioner in the tensioning rotary direction.

2. The instrument of claim 1 wherein the living hinge portion includes a base portion and an elongate arm portion extending away from the base portion toward the pawl portion.

3. The instrument of claim 1 wherein the body includes a through opening extending along opposite sides of the living hinge portion and about the pawl portion to define an outer periphery of the pawl portion and the living hinge portion.

4. The instrument of claim 1 wherein the body includes a second living hinge portion and a second pawl portion supported by the second living hinge portion and configured to be received at least partially in one of the recesses of the ratchet gear, the second living hinge portion configured to permit the second pawl portion to be shifted out of the one recess and at least partially into an adjacent one of the recesses of the ratchet gear with turning of the rotary tensioner in the tensioning rotary direction.

5. The instrument of claim 4 wherein the pawl portions and living hinge portions are configured so that one of the pawl portions is always received at least partially in one of the recesses of the ratchet gear to resist turning of the rotary tensioner in a pay out rotary direction.

6. The instrument of claim 1 wherein the body has a one-piece construction so that the living hinge portion and the pawl portion are integrally formed.

7. The instrument of claim 6 wherein the rotary tensioner includes a handle fixed relative to the ratchet gear and the rotary tensioner has a one-piece construction.

8. The instrument of claim 6 wherein the body is of a plastic material.

9. The instrument of claim 1 wherein the body includes a cavity and the rotary tensioner is at least partially in the cavity.

10. The instrument of claim 1 wherein the ratchet gear includes a plurality of ratchet teeth that define the plurality of recesses therebetween wherein each of the ratchet teeth includes a ramp surface operable to shift the pawl portion radially outward and flex the living hinge portion with turning of the rotary tensioner in the tensioning rotary direction.

11. The instrument of claim 1 further comprising a guide connected to the body at a swivel connection and having a through passage sized to receive a surgical cable.

12. The instrument of claim 11 further comprising a cutting blade mounted to the guide and an actuator operable to shift the cutting blade relative to the guide and cut a surgical cable.

13. An instrument for tensioning a surgical cable, the instrument comprising:
a one-piece body having a cavity;
a rotary tensioner at least partially in the cavity and rotatable relative to the body in a tensioning rotary direction to wind a surgical cable onto the rotary tensioner;
ratchet portions of the one-piece body and the rotary tensioner configured to permit the rotary tensioner to turn in the tensioning rotary direction and resist turning of the rotary tensioner in an opposite, pay out rotary direction.

14. The instrument of claim 13 wherein the ratchet portions include a pawl portion of the one-piece body and a ratchet gear of the rotary tensioner.

15. The instrument of claim 13 wherein the ratchet portions include a first pawl portion and a second pawl portion of the one-piece body and a ratchet gear of the rotary tensioner.

16. The instrument of claim 13 wherein the ratchet portions include a pawl portion of the one-piece body and the one-piece body includes a living hinge connected to the pawl portion that permits the pawl to pivot relative to the rotary tensioner.

17. The instrument of claim 13 further comprising a tubular member connected to the one-piece body at a swivel connection and having a through passage sized to receive a surgical cable.

18. The instrument of claim 17 further comprising a cutting blade mounted to the tubular member and an actuator operable to shift the cutting blade relative to the tubular member and cut a surgical cable.

19. A method of tensioning a surgical cable, the method comprising:
turning a rotary tensioner in a tensioning direction relative to a body to wind a surgical cable onto the rotary tensioner; and
flexing a living hinge of the body to permit a pawl portion of the body to shift from a first recess to a second recess of the rotary tensioner.

20. The method of claim 19 wherein flexing the living hinge of the body includes cammingly engaging the pawl portion of the body with a tooth of the rotary tensioner to shift the pawl portion out of the first recess of the rotary tensioner.

* * * * *